(12) United States Patent
Muroyama et al.

(10) Patent No.: US 9,450,186 B2
(45) Date of Patent: Sep. 20, 2016

(54) 6,12-DIOXAANTHANTHRENE DERIVATIVE, ORGANIC SEMICONDUCTOR ELEMENT, AND METHOD FOR MANUFACTURING ORGANIC SEMICONDUCTOR ELEMENT

(71) Applicant: SONY CORPORATION, Tokyo (JP)

(72) Inventors: Masakazu Muroyama, Kanagawa (JP); Norihito Kobayashi, Kanagawa (JP); Eri Igarashi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 14/425,584

(22) PCT Filed: Aug. 27, 2013

(86) PCT No.: PCT/JP2013/072841
§ 371 (c)(1),
(2) Date: Mar. 3, 2015

(87) PCT Pub. No.: WO2014/042001
PCT Pub. Date: Mar. 20, 2014

(65) Prior Publication Data
US 2015/0228898 A1    Aug. 13, 2015

(30) Foreign Application Priority Data

Sep. 11, 2012    (JP) .................................. 2012-199497

(51) Int. Cl.
*H01L 51/00* (2006.01)
*C07D 493/06* (2006.01)
(Continued)

(52) U.S. Cl.
CPC ........... *H01L 51/004* (2013.01); *C07D 493/06* (2013.01); *C07D 493/22* (2013.01); *C08F 124/00* (2013.01); *H01L 51/0035* (2013.01);
(Continued)

(58) Field of Classification Search
CPC ............... H01L 51/004; H01L 29/786; H01L 51/0035; H01L 51/0001; H01L 51/001; H01L 51/0073; H01L 51/0545; H01L 51/0558; C07D 493/06; C07D 493/22; C08F 124/00
USPC .......................................................... 438/99
See application file for complete search history.

(56) References Cited

U.S. PATENT DOCUMENTS

2012/0025173 A1*   2/2012   Kobayashi .......... H01L 51/0003
                                                                257/40

FOREIGN PATENT DOCUMENTS

JP          2010-6794 A       1/2010
JP          2010-232368      10/2010
(Continued)

OTHER PUBLICATIONS

International Search Report prepared by the Japanese Patent Office on Nov. 12, 2013, for International Application No. PCT/JP2013/072841.

*Primary Examiner* — Fernando L Toledo
*Assistant Examiner* — Adam S Bowen
(74) *Attorney, Agent, or Firm* — Chip Law Group

(57) ABSTRACT

There are provided a 6,12-dioxaanthanthrene derivative which is an organic semiconductor material capable of improving resistance to mechanical deformation, an organic semiconductor element, and a method for manufacturing the organic semiconductor element. The 6,12-dioxaanthanthrene derivative is represented by structural formula (1). $R^3$ and $R^9$ are photopolymerizable unsaturated groups. $R^5$ and $R^{11}$ are non-photopolymerizable substituents.

9 Claims, 5 Drawing Sheets

(51) Int. Cl.
*C07D 493/22* (2006.01)
*C08F 124/00* (2006.01)
*H01L 51/05* (2006.01)

(52) U.S. Cl.
CPC .......... *H01L 51/0001* (2013.01); *H01L 51/001* (2013.01); *H01L 51/0073* (2013.01); *H01L 51/0545* (2013.01); *H01L 51/0558* (2013.01)

(56) References Cited

FOREIGN PATENT DOCUMENTS

| | | |
|---|---|---|
| JP | 2012-12495 A | 1/2012 |
| JP | 2012-19132 A | 1/2012 |

\* cited by examiner

6,12-DIOXAANTHANTHRENE DERIVATIVE, ORGANIC SEMICONDUCTOR ELEMENT, AND METHOD FOR MANUFACTURING ORGANIC SEMICONDUCTOR ELEMENT

CROSS REFERENCE TO RELATED APPLICATIONS

This application is a national stage application under 35 U.S.C. 371 and claims the benefit of PCT Application No. PCT/JP2013/072841 having an international filing date of Aug. 27, 2013, which designated the United States, which PCT application claimed the benefit of Japanese Patent Application No. 2012-199497 filed Sep. 11, 2012, the disclosures of both the above-identified applications are incorporated herein by reference.

TECHNICAL FIELD

This disclosure relates to a 6,12-dioxaanthanthrene derivative, an organic semiconductor element, and a method for manufacturing the organic semiconductor element.

BACKGROUND ART

For a semiconductor layer of a semiconductor element, inorganic semiconductor materials such as a silicon compound or a gallium compound are widely used. Meanwhile, a polycyclic aromatic compound described in Patent Document 1 exhibits physical properties as a semiconductor due to an interaction between molecules, and attracts attention as a semiconductor layer-forming material which may replace an inorganic semiconductor material.

SUMMARY OF THE INVENTION

A semiconductor material is also applied to a device which requires mechanical flexibility, such as a flexible display device. Therefore, in an organic semiconductor material used for a semiconductor layer of a semiconductor element, it is desired to improve resistance to mechanical deformation.

Accordingly, it is desired to provide a 6,12-dioxaanthanthrene derivative which is an organic semiconductor material capable of improving resistance to mechanical deformation, an organic semiconductor element, and a method for manufacturing the organic semiconductor element.

A 6,12-dioxaanthanthrene derivative according to an embodiment of the technology of this disclosure is a 6,12-dioxaanthanthrene derivative represented by structural formula (1):

[chemical formula 1]

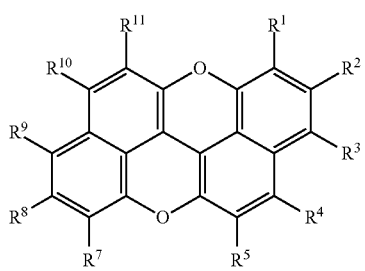

(1)

$R^3$ and $R^9$ are photopolymerizable unsaturated groups. $R^5$ and $R^{11}$ are non-photopolymerizable substituents.

An organic semiconductor element according to an embodiment of the technology of this disclosure includes an organic semiconductor layer. The organic semiconductor layer includes a polymer of the 6,12-dioxaanthanthrene derivative represented by structural formula (1):

[chemical formula 2]

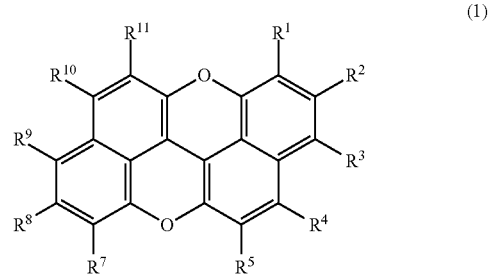

(1)

$R^3$ and $R^9$ are photopolymerizable unsaturated groups. $R^5$ and $R^{11}$ are non-photopolymerizable substituents.

The organic semiconductor element according to an embodiment of the technology of this disclosure includes an organic semiconductor layer. The organic semiconductor layer includes an organic semiconductor material which has a repeating unit of a 6,12-dioxaanthanthrene derivative represented by structural formula (2):

[chemical formula 3]

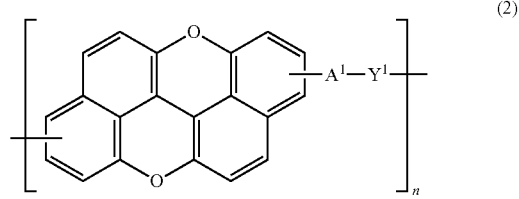

(2)

$A^1$ represents an aromatic ring, a heteroaromatic ring, or a direct bond. $Y^1$ represents any one of a divalent alkene, a divalent alkyne, an azo group, and a triazole ring.

In a method for manufacturing an organic semiconductor element according to an embodiment of the technology of this disclosure, a monomer layer is formed, and the monomer layer is irradiated with light to form an organic semiconductor layer. The monomer layer includes the 6,12-dioxaanthanthrene derivative represented by structural formula (1):

[chemical formula 4]

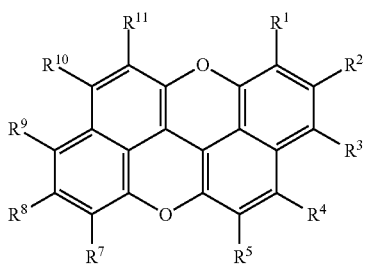

(1)

$R^3$ and $R^9$ are photopolymerizable unsaturated groups. $R^5$ and $R^{11}$ are non-photopolymerizable substituents.

According to an embodiment of the technology of this disclosure, since the 6,12-dioxaanthanthrene derivative which is a polycyclic aromatic compound forms a polymer, resistance of the organic semiconductor element to mechanical deformation is improved.

MODE FOR CARRYING OUT THE INVENTION

An embodiment of the technology of this disclosure will be described with reference to FIGS. 1 to 9.

[6,12-Dioxaanthanthrene Derivative]

A 6,12-dioxaanthanthrene derivative is a compound represented by structural formula (1), and contains 6,12-dioxaanthanthrene (peri-xanthenoxanthene) as a matrix. At least one of $R^1$, $R^2$, $R^3$, $R^4$, $R^5$, $R^7$, $R^8$, $R^9$, $R^{10}$, and $R^{11}$ contains a photopolymerizable unsaturated group.

[chemical formula 5]

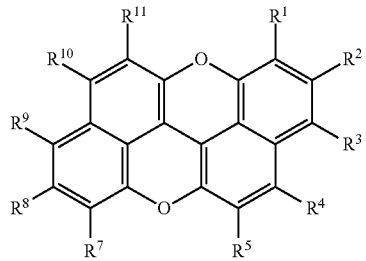

(1)

The photopolymerizable unsaturated group is an unsaturated group which generates a radical by irradiation with light. The photopolymerizable unsaturated group generates a radical by irradiation with at least one of infrared light, visible light, ultraviolet light, ion beam, and radiation. The photopolymerizable unsaturated group may be a monovalent unsaturated group containing either a double bond or a triple bond, or may be a divalent unsaturated group containing a double bond and/or a triple bond. The photopolymerizable unsaturated group may contain a double bond in a resonance structure and a triple bond in a resonance structure. The photopolymerizable unsaturated group is, for example, at least one of an alkenyl group, an alkynyl group, a diynyl group, a methacrylic group, an ethyl methacrylic group, a diazo group, and an azido group.

Figure 1:
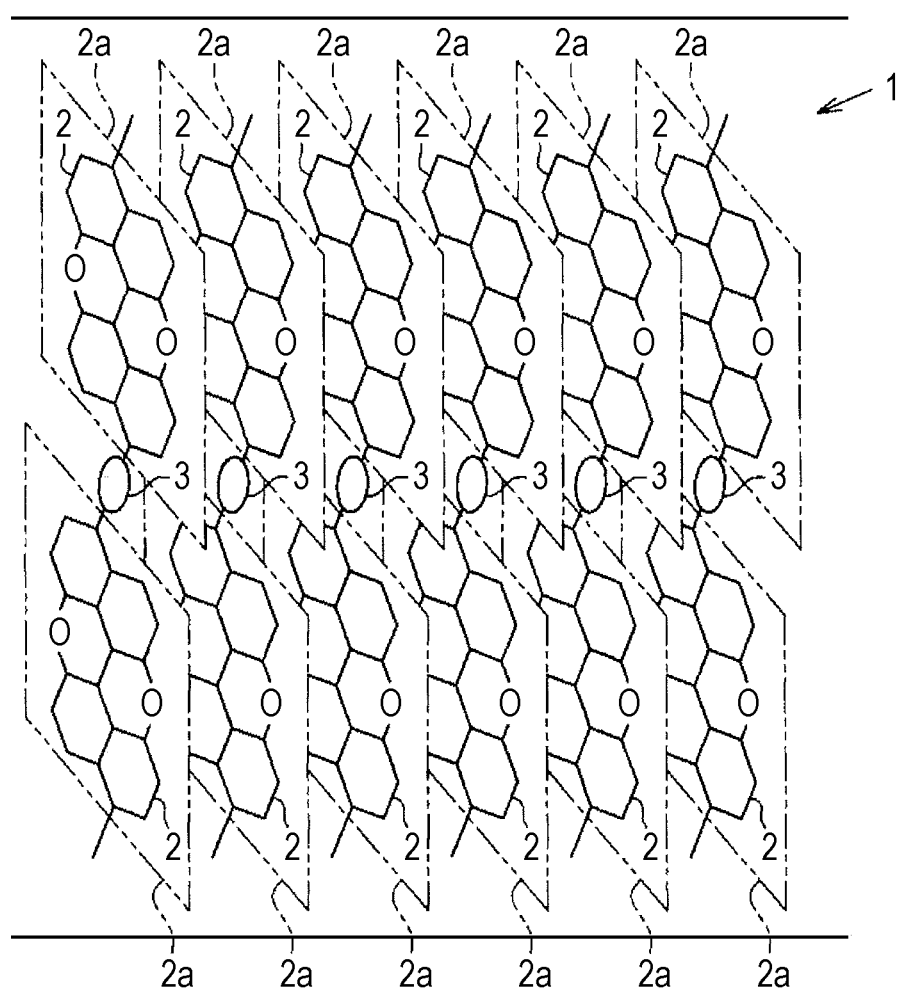
FIG. 1 is a view schematically illustrating an extent of π conjugation in a polymer of a 6,12-dioxaanthanthrene derivative according to an embodiment of the technology of this disclosure.
Figure 2:
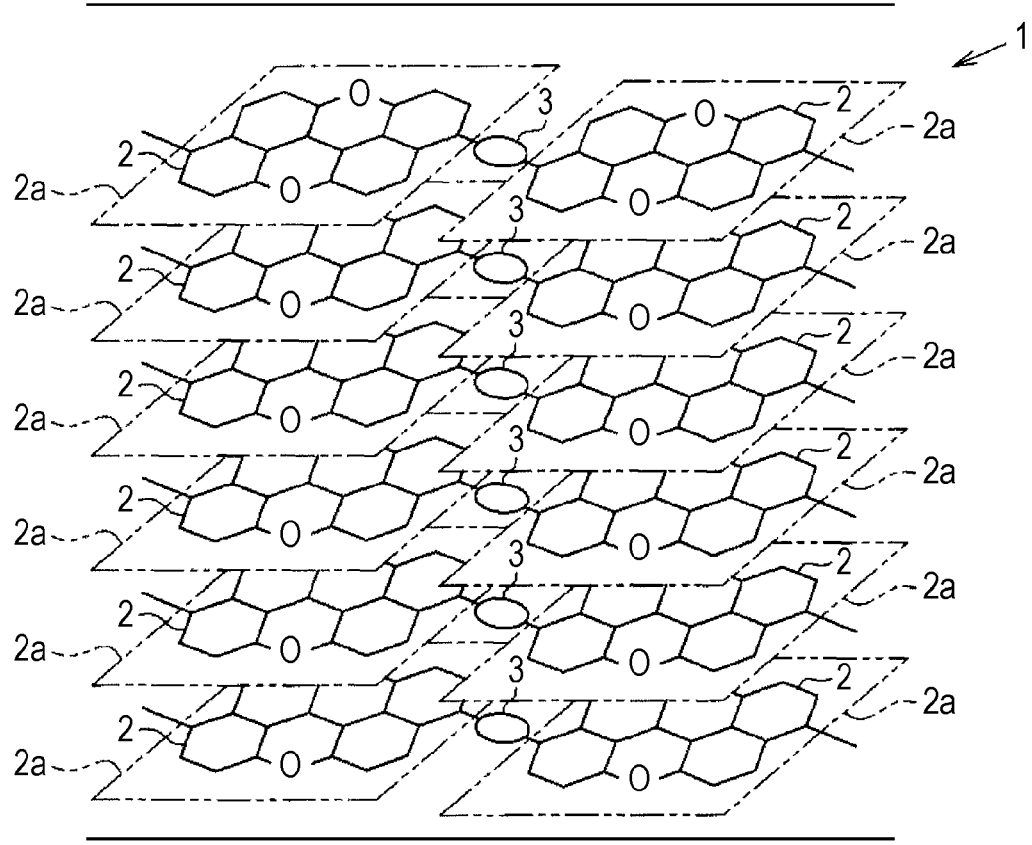
FIG. 2 is a view schematically illustrating an extent of π conjugation in the polymer of the 6,12-dioxaanthanthrene derivative according to the embodiment of the technology of this disclosure.

In an organic semiconductor layer, for example, two different 6,12-dioxaanthanthrenes are aligned in a direction perpendicular to a π conjugation plane formed in the molecule, and are also aligned in a direction parallel to the π conjugation plane formed in the molecule. In the 6,12-dioxaanthanthrenes which are aligned in the direction perpendicular to the π conjugation plane in the molecule, planes on which π conjugation is formed face each other, and therefore conductivity between the molecules is enhanced. The 6,12-dioxaanthanthrenes which are aligned along the π conjugation plane in the molecule are polymerized via a photopolymerizable unsaturated group, and therefore conductivity between the molecules is enhanced. In the organic semiconductor layer, for example, the 6,12-dioxaanthanthrene derivatives are aligned as illustrated in FIG. 1 or 2. The organic semiconductor layer has a planar shape constituted by a surface which is greater than the thickness.

As illustrated in FIG. 1, in the organic semiconductor layer 1, multiple repeating units 2 in a polymer are arranged while a π conjugation plane 2a of each repeating unit 2 is inclined to a surface of the organic semiconductor layer 1. One repeating unit 2 is coupled, through a coupling portion 3, to another repeating unit 2 which is adjacent in a direction where the repeating units 2 are inclined to the surface of the organic semiconductor layer 1. The coupling portion 3 contains an atom constituting a photopolymerizable unsaturated group of a 6,12-dioxaanthanthrene derivative. In the organic semiconductor layer 1, in a case where the repeating units 2 aligned in a direction along the surface of the organic semiconductor layer 1 are set as one layer, several layers to about ten layers of the repeating unit 2 are laminated.

As described above, when the π conjugation plane 2a is inclined to the surface of the organic semiconductor layer 1, in a case where the direction along the surface of the organic semiconductor layer 1 is set as a direction in which carriers flow, the π conjugation between the molecules in the polymer contributes to movement of the carriers.

As illustrated in FIG. 2, in the organic semiconductor layer 1, multiple repeating units 2 in the polymer are arranged while the π conjugation plane 2a of each repeating unit 2 is extended along the surface of the organic semiconductor layer 1. One repeating unit 2 is coupled, through the coupling portion 3, to another repeating unit 2 which is adjacent in a plane direction of the organic semiconductor layer 1. In the organic semiconductor layer 1, in a case where the repeating units 2 aligned in a direction along the surface of the organic semiconductor layer 1 are set as one layer, several layers to about ten layers of the repeating unit 2 are laminated.

As described above, when the π conjugation plane 2a is extended along the surface of the organic semiconductor layer 1, in a case where the direction along the surface of the organic semiconductor layer 1 is set as a direction in which carriers flow, the π conjugation in the molecule of the polymer contributes to movement of the carriers. Therefore, the degree of movement of the carriers is enhanced compared to the π conjugation plane 2a which is inclined to the surface of the organic semiconductor layer 1.

When the photopolymerizable unsaturated group is a diazo group or an azido group, the photopolymerizable unsaturated group contains a nitrogen atom having an unpaired electron. When a nitrogen atom is contained in the coupling portion 3, the nitrogen atom functions as an electron-providing portion which can increase the electron density of the repeating unit 2. Accordingly, the π conjugation between the repeating units 2 is enhanced between the polymers. In addition, when the nitrogen atom contained in the coupling portion 3 constitutes an unsaturated bond, the π conjugation between the repeating units 2 is enhanced in the polymer.

In order to enhance the conductivity between the molecules, it is preferable that a distance between two polymerized 6,12-dioxaanthanthrenes be short. In addition, it is preferable that a multiple bond be formed between the two 6,12-dioxaanthanthrenes. When the photopolymerizable unsaturated group is an alkenyl group, the photopolymerizable unsaturated group is preferably a vinyl group having two carbon atoms. When the photopolymerizable unsaturated group is an alkynyl group, the photopolymerizable unsaturated group preferably has three or less carbon atoms, and more preferably is an ethynyl group having two carbon atoms.

In the 6,12-dioxaanthanthrene derivative, when one of $R^1$ to $R^{11}$ (except $R^6$) is a photopolymerizable unsaturated group, the photopolymerizable unsaturated group is most preferably $R^3$, and in succession, is preferably $R^2$, $R^4$, $R^1$, and $R^5$ in this order.

In the 6,12-dioxaanthanthrene derivative, when two of $R^1$ to $R^{11}$ (except $R^6$) are photopolymerizable unsaturated groups, the photopolymerizable unsaturated groups are most preferably $R^3$ and $R^9$, and in succession, are preferably $R^2$ and $R^8$, $R^4$ and $R^{10}$, $R^1$ and $R^7$, and $R^5$ and $R^{11}$ in this order.

A 6,12-dioxaanthanthrene derivative in which $R^3$ among $R^1$ to $R^{11}$ (except $R^6$) is a photopolymerizable unsaturated group and the other functional groups are independently hydrogen atoms, for example, is generated via a substitution reaction of a bromine atom from a 6,12-dioxaanthanthrene bromide in which $R^3$ is a bromine atom. A 6,12-dioxaanthanthrene derivative in which $R^3$ and $R^9$ among $R^1$ to $R^{11}$ (except $R^6$) are photopolymerizable unsaturated groups and the other functional groups are independently hydrogen atoms, for example, is generated via a substitution reaction of a bromine atom from a 6,12-dioxaanthanthrene bromide in which $R^3$ and $R^9$ are bromine atoms.

At this time, the 6,12-dioxaanthanthrene bromide is obtained by a ring closure reaction in a molecule with a 1,1'-bis-2-naphthol derivative. For example, 6,6'-dibromo-1,1'-bis-2-naphthol dissolved in a sodium hydroxide aqueous solution is oxidized in the air after addition of a copper acetate aqueous solution, thereby obtaining a 6,12-dioxaanthanthrene bromide. In a case where the photopolymerizable unsaturated groups are $R^3$ and $R^9$, steric hindrance is suppressed in a ring closure reaction in a molecule of the 1,1'-bis-2-naphthol derivative compared to a case where the photopolymerizable unsaturated group is at another position. In addition, in a case where the photopolymerizable unsaturated groups are $R^3$ and $R^9$, a distance between crosslinking points is long in a molecule of the 6,12-dioxaanthanthrene derivative. As a result, steric hindrance between the 6,12-dioxaanthanthrene derivatives is suppressed in polymerization of the 6,12-dioxaanthanthrene derivative. Accordingly, a polymerization reaction between the 6,12-dioxaanthanthrene derivatives easily proceeds. In the polymer of the 6,12-dioxaanthanthrene derivative, a π conjugation system for each 6,12-dioxaanthanthrene derivative greatly contributes to a π conjugation system of the polymer.

The substitution reaction of a bromine atom with a photopolymerizable unsaturated group may be performed before the ring closure reaction in a molecule with the 1,1'-bis-2-naphthol derivative. When the substitution reaction with a photopolymerizable unsaturated group is performed before the ring closure reaction, it is possible to suppress a reaction between the photopolymerizable unsaturated group and a cyclization reaction point. For example, a 6,12-dioxaanthanthrene derivative in which $R^2$ and $R^8$ are photopolymerizable unsaturated groups can also be generated by the same method as in the case where $R^3$ and $R^9$ are photopolymerizable unsaturated groups.

Substituents of $R^1$ to $R^{11}$ (except $R^6$) other than the photopolymerizable unsaturated group may be non-photopolymerizable substituents other than a hydrogen atom. In a case where $R^3$ and $R^9$ are photopolymerizable unsaturated groups, $R^5$ and $R^{11}$, or $R^1$ and $R^7$ are non-photopolymerizable substituents, whereby steric hindrance between the photopolymerizable unsaturated group and the non-photopolymerizable substituent can be suppressed. The non-photopolymerizable substituent may be, for example, an alkyl group, a cycloalkyl group, an aryl group, an arylalkyl group, a heteroaromatic ring group, a heterocyclic group, an alkoxy group, a cycloalkoxy group, an aryloxy group, an alkylthio group, or a cycloalkylthio group. The non-photopolymerizable substituent may be an arylthio group, an alkoxycarbonyl group, an aryloxycarbonyl group, a sulfamoyl group, an acyl group, an acyloxy group, an amide group, a carbamoyl group, an ureido group, a sulfinyl group, an alkylsulfonyl group, an arylsulfonyl group, or an amino group. The non-photopolymerizable substituent may be a halogen atom, a fluorohydrocarbon group, a cyano group, a nitro group, a hydroxy group, a mercapto group, or a silyl group.

The alkyl group is a methyl group, an ethyl group, a propyl group, an isopropyl group, a t-butyl group, a penthyl group, a hexyl group, an octyl group, a dodecyl group, or the like. The alkyl group may have a linear chain shape or a branched chain shape including a main chain and aside chain. The cycloalkyl group is a cyclopenthyl group, a cyclohexyl group, or the like. The aryl group is a phenyl group, a naphthyl group, a biphenyl group, or the like. The arylalkyl group is a methylaryl group, an ethylaryl group, an isopropylaryl group, a normal butylaryl group, a p-tolyl group, a p-ethylphenyl group, a p-isopropylphenyl group, a 4-propylphenyl group, a 4-butylphenyl group, a 4-nonylphenyl group, or the like.

The heteroaromatic ring group is a pyridyl group, a thienyl group, a furyl group, a pyridazinyl group, a pyrimidinyl group, a pyrazinyl group, a triazinyl group, an imidazolyl group, a pyrazolyl group, a thiazolyl group, a quinazolinyl group, a phthalazinyl group, or the like. The heterocyclic group is a pyrrolidyl group, an imidazolidyl group, a morpholyl group, an oxazolidyl group, or the like. The alkoxy group is a methoxy group, an ethoxy group, a propyloxy group, a penthyloxy group, a hexyloxy group, or the like. The cycloalkoxy group is a cyclopenthyloxy group, a cyclohexyloxy group, or the like. The aryloxy group is a phenoxy group, a naphthyloxy group, or the like. The alkylthio group is a methylthio group, an ethylthio group, a propylthio group, a penthylthio group, a hexylthio group, or the like.

The cycloalkylthio group is a cyclopenthylthio group, a cyclohexylthio group, or the like. The arylthio group is a phenylthio group, a naphthylthio group, or the like. The alkoxycarbonyl group is a methyloxycarbonyl group, an ethyloxycarbonyl group, a butyloxycarbonyl group, an octyloxycarbonyl group, or the like. The aryloxycarbonyl group is a phenyloxycarbonyl group, a naphthyloxycarbonyl group, or the like. The sulfamoyl group is an aminosulfonyl group, a methyl aminosulfonyl group, a dimethyl aminosulfonyl group, a cyclohexylaminosulfonyl group, a phenyl aminosulfonyl group, a naphthyl aminosulfonyl group, a 2-pyridyl aminosulfonyl group, or the like.

The acyl group is an acetyl group, an ethyl carbonyl group, a propyl carbonyl group, a cyclohexyl carbonyl group, an octyl carbonyl group, a 2-ethylhexyl carbonyl group, a dodecyl carbonyl group, a phenyl carbonyl group, a naphthyl carbonyl group, a pyridyl carbonyl group, or the like. The acyloxy group is an acetyloxy group, an ethyl carbonyloxy group, an octyl carbonyloxy group, a phenyl carbonyloxy group, or the like.

The amide group is a methyl carbonylamino group, an ethyl carbonylamino group, a dimethyl carbonylamino group, a penthyl carbonylamino group, a cyclohexyl carbonylamino group, a 2-ethylhexyl carbonylamino group, a phenyl carbonylamino group, a naphthyl carbonylamino group, or the like. The carbamoyl group is an aminocarbonyl group, a methyl aminocarbonyl group, a dimethyl aminocarbonyl group, a cyclohexyl aminocarbonyl group, a 2-ethylhexyl aminocarbonyl group, a phenyl aminocarbonyl group, a naphthyl aminocarbonyl group, a 2-pyridyl aminocarbonyl group, or the like. The ureido group is a methyl ureido group, an ethyl ureido group, a cyclohexyl ureido group, a dodecyl ureido group, a phenyl ureido group, a naphthyl ureido group, a 2-pyridylamino ureido group, or the like.

The sulfinyl group is a methylsulfinyl group, an ethylsulfinyl group, a butylsulfinyl group, a cyclohexylsulfinyl group, a 2-ethylhexylsulfinyl group, a phenylsulfinyl group, a naphthylsulfinyl group, a 2-pyridylsulfinyl group, or the like. The alkylsulfonyl group is a methylsulfonyl group, an ethylsulfonyl group, a butylsulfonyl group, a cyclohexylsulfonyl group, a dodecylsulfonyl group, a 2-ethylhexylsulfonyl group, a dodecylsulfonyl group, or the like. The arylsulfonyl group is a phenylsulfonyl group, a naphthylsulfonyl group, a 2-pyridylsulfonyl group, or the like.

The amino group is an amino group, an ethylamino group, a dimethylamino group, a butylamino group, a 2-ethylhexylamino group, an anilino group, a naphthylamino group, a 2-pyridylamino group, or the like. The halogen atom is a fluorine atom, a chlorine atom, a bromine atom, or an iodine atom. The fluorohydrocarbon group is a fluoromethyl group, a trifluoromethyl group, a pentafluoroethyl group, a pentafluorophenyl group, or the like. The silyl group is a trimethyl silyl group, triisopropyl silyl group, a triphenyl silyl group, a phenyldiethyl silyl group, or the like.

In the non-photopolymerizable substituent, one or more hydrogen atoms may be further substituted with the same non-photopolymerizable substituent or a different non-photopolymerizable substituent. Multiple non-photopolymerizable substituents may be bonded to each other to form a cyclic substituent.

The photopolymerizable unsaturated group and the non-photopolymerizable substituent preferably have a thienyl group, a pyridyl group, a naphthyl group, and a phenyl group. With these substituents, π conjugation in the polymer of the 6,12-dioxaanthanthrene derivative is enhanced. Accordingly, an electron mobility in the organic semiconductor layer including the polymer of the 6,12-dioxaanthanthrene derivative is enhanced. Particularly, it is more preferable that the non-photopolymerizable substituent be a thienyl group because an electron distribution in the polymer is uniformized by a sulfur atom contained in the thienyl group.

In the 6,12-dioxaanthanthrene derivative, when one of $R^1$ to $R^{11}$ (except $R^6$) is a non-photopolymerizable substituent, two of $R^1$ to $R^{11}$ (except $R^6$) are photopolymerizable unsaturated groups, and the other functional groups are independently hydrogen atoms, the non-photopolymerizable substituent is preferably $R^3$ or $R^9$. One of the two photopolymerizable unsaturated groups is preferably $R^3$ or $R^9$ which is a functional group different from the non-photopolymerizable substituent. The other one is preferably $R^5$ or $R^{11}$ which is a functional group similar to the non-photopolymerizable substituent. Accordingly, steric hindrance between the non-photopolymerizable substituent and the two photopolymerizable unsaturated groups is suppressed. In the polymer of the 6,12-dioxaanthanthrene derivative, since a distance between crosslinking points is long in the 6,12-dioxaanthanthrene derivative, a photopolymerization reaction between the 6,12-dioxaanthanthrene derivatives easily proceeds.

In the 6,12-dioxaanthanthrene derivative, when two of $R^1$ to $R^{11}$ (except $R^6$) are non-photopolymerizable substituents, two of $R^2$ to $R^{11}$ (except $R^6$) are photopolymerizable unsaturated groups, and the other functional groups are independently hydrogen atoms, the non-photopolymerizable substituents are preferably $R^3$ and $R^9$. The two photopolymerizable unsaturated groups are preferably any pair of $R^4$ and $R^{10}$, $R^2$ and $R^8$, $R^1$ and $R^7$, and $R^5$ and $R^{11}$.

In a functional group containing a photopolymerizable unsaturated group of $R^1$ to $R^{11}$ (except $R^6$) in the 6,12-dioxaanthanthrene derivative, the 6,12-dioxaanthanthrene as a matrix and the photopolymerizable unsaturated group may be bonded through an aromatic ring or a heteroaromatic ring in the non-photopolymerizable substituent. The heteroaromatic ring is preferably a thienyl group, a pyridyl group, a phenyl group, or a naphthyl group. In this case, the more easily the substitution of the photopolymerizable unsaturated group proceeds, the more preferable the position of the carbon atom into which the photopolymerizable unsaturated group is introduced in the aromatic ring or the heteroaromatic ring is. For example, in the thienyl group, the photopolymerizable unsaturated group is introduced into the carbon atom most preferably at the 1-position, and in succession preferably at the 2-position or the 3-position. In the pyridyl group, the photopolymerizable unsaturated group is introduced into the carbon atom most preferably at the 1-position, and in succession preferably at the 3-position, the 2-position, and the 4-position in this order. In the naphthyl group, the photopolymerizable unsaturated group is introduced into the carbon atom most preferably at the 4-position, in succession preferably at the 3-position, and in succession preferably at the 1-position, the 2-position, the 5-position, the 6-position, or the 7-position. In the phenyl group, the photopolymerizable unsaturated group is introduced into the carbon atom most preferably at the 3-position, in succession preferably at the 2-position or the 4-position, and in succession preferably at the 1-position or the 5-position.

For example, a 6,12-dioxaanthanthrene derivative in which $R^5$ and $R^{11}$ are non-photopolymerizable substituents is generated, for example, through a substitution reaction of a bromine atom from a 6,12-dioxaanthanthrene bromide in which $R^5$ and $R^{11}$ are bromine atoms. When a 6,12-dioxaanthanthrene bromide is obtained through a ring closure reaction in a molecule with a 1,1'-bis-2-naphthol derivative, a substitution reaction of a bromine atom with a non-photopolymerizable substituent may be performed before or after the ring closure reaction. When the ring closure reaction is performed before the substitution reaction, it is possible to suppress a reaction between the non-photopolymerizable substituent and a cyclization reaction point.

[Organic Semiconductor Element]

An organic semiconductor element which includes an organic semiconductor layer containing a polymer of a 6,12-dioxaanthanthrene derivative will be described with reference to FIG. 3.

Figure 3:
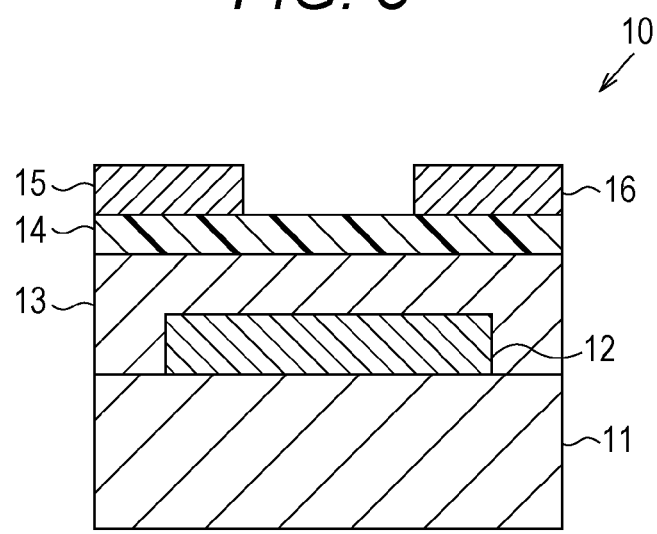
FIG. 3 is a view illustrating a cross-sectional structure of an organic semiconductor element according to the embodiment of the technology of this disclosure.

As illustrated in FIG. 3, in an organic semiconductor element 10, a whole gate electrode 12 formed on a part of a substrate 11 is covered with a gate insulating layer 13. An organic semiconductor layer 14 is laminated on the gate insulating layer 13. A source electrode 15 and a drain electrode 16 are independently formed on parts of the organic semiconductor layer 14. The organic semiconductor element 10 is a bottom-gate/top-contact type organic semiconductor transistor.

An inorganic material or an organic material is used for a forming material of the substrate 11. Each of an inorganic material and an organic material may be used alone. Alternatively, a layer formed of an inorganic material and a layer formed of an organic material may be laminated on each other. Examples of the inorganic material include silicon, spin-on glass, silicon nitride, aluminum oxide, and a high dielectric constant insulating material of a metal oxide. When silicon is used for the forming material of the substrate 11, a surface of the substrate 11 on which the gate insulating layer 13 is laminated is preferably oxidized. Examples of the organic material include polymers such as polymethyl methacrylate, polyvinyl alcohol, polyvinyl phenol, polyether ketone, polyimide, polycarbonate, polyethylene terephthalate, and polyethylene naphthalate.

An inorganic material and an organic material are used for a forming material of the gate electrode 12. The inorganic material includes a metal material and a nonmetal material. Examples of the metal material include gold, platinum, palladium, chromium, molybdenum, nickel, aluminum, silver, tantalum, tungsten, copper, titanium, indium, and tin. The metal material may be an alloy including two or more of these metals, or a conductive particle formed of a metal or an alloy. The nonmetal material is a conductive material including impurities, such as polysilicon. The organic material is a conductive polymer such as poly(3,4-ethylene dioxythiophene) and polystyrene sulfonic acid. The gate electrode 12 may have a single layer formed of any one of a metal material, a nonmetal material, and an organic material, or may have a structure in which single layers different from each other are laminated on each other.

An organic insulating material and an inorganic insulating material are used for the forming material of the gate insulating layer 13. Examples of the organic insulating material include polymethyl silsesquioxane, polymethyl methacrylate, polyvinyl phenol, and polyvinyl alcohol. A combination of these polymers may be used for the organic insulating material.

Examples of the inorganic insulating material include a silicon oxide material, a silicon nitride material, and a high dielectric constant insulating material of a metal oxide. Examples of the silicon oxide material include silicon oxide, BPSG, PSG, BSG, AsSG, PbSG, silicon oxide nitride, SOG, and a silicon-based low dielectric constant material.

A polymer of a 6,12-dioxaanthanthrene derivative is used for the forming material of the organic semiconductor layer 14. A doping material of n-type impurities or a doping material of p-type impurities may be added to the forming material of the organic semiconductor layer 14.

A similar material to that of the gate electrode 12 is used for the forming material of the source electrode 15 and the forming material of the drain electrode 16. The forming materials of the gate electrode 12, the source electrode 15, and the drain electrode 16 may be the same as or different from each other.

[Method for Manufacturing Organic Semiconductor Element]

A method for manufacturing an organic semiconductor element will be described with reference to FIGS. 4 to 9.

Figure 4:
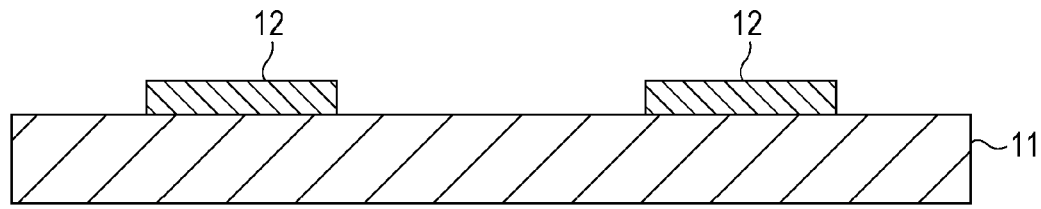
FIG. 4 is a manufacturing process view for illustrating a method for manufacturing an organic semiconductor element according to the embodiment of this disclosure.

As illustrated in FIG. 4, when the organic semiconductor element 10 is manufactured, first, the gate electrode 12 is formed on the substrate 11. A film formation method such as a PVD method, a CVD method, a spin coat method, a printing method, a coating method, a stamp method, a plating method, and a spray method is used to form the gate electrode 12.

Figure 5:
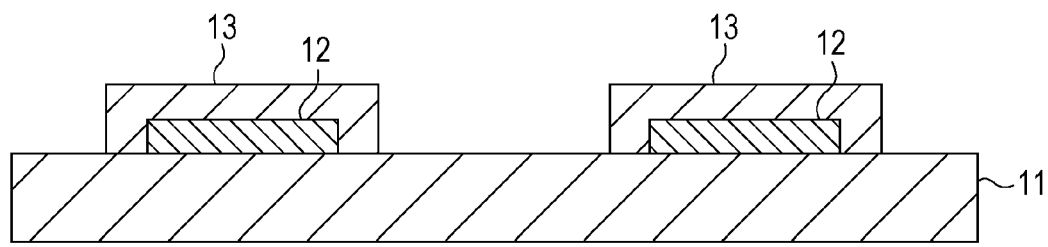
FIG. 5 is a manufacturing process view for illustrating the method for manufacturing an organic semiconductor element according to the embodiment of this disclosure.

As illustrated in FIG. 5, after the gate electrode 12 is formed, the gate insulating layer 13 covering the gate electrode 12 is formed. Various film formation methods are used to form the gate insulating layer 13 in a similar manner to forming the gate electrode 12. The gate insulating layer 13 can be also formed by oxidation or nitration to a surface of the gate electrode 12. An oxidation method with oxygen plasma, an anodic oxidation method, or the like is used to oxidize the surface of the gate electrode 12. A nitration method with nitrogen plasma or the like is used to nitride the surface of the gate electrode 12.

Figure 6:
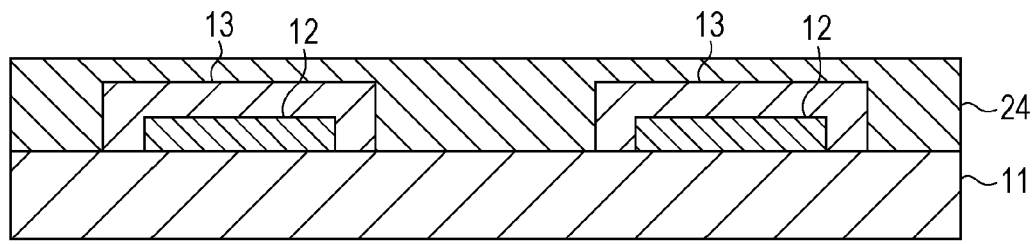
FIG. 6 is a cross-sectional elevation view for illustrating the method for manufacturing an organic semiconductor element according to the embodiment of this disclosure.

As illustrated in FIG. 6, after the gate insulating layer 13 is formed, a monomer layer 24 covering the gate insulating layer 13 is formed on the whole substrate 11. The monomer layer 24 includes a 6,12-dioxaanthanthrene derivative as a monomer. The monomer layer 24 may include a polymerization initiator, and may further include a polymerization accelerator.

For the polymerization initiator, a radical-type photopolymerization initiator, an alkylphenon-type photopolymerization initiator, an acylphosphine oxide-type photopolymerization initiator, a titanocene-type photopolymerization initiator, another photopolymerization initiator, or the like is used.

Examples of the alkylphenon-type photopolymerization initiator include 2,2-dimethoxy-1,2-diphenylethan-1-one, 1-hydroxy-cyclohexyl-phenyl-ketone, 2-hydroxy-2-methyl-1-phenyl-propan-1-one, 1-[4-(2-hydroxyethoxy)-phenyl]-2-hydroxy-2-methyl-1-propan-1-one, 2-hyrodoxy-1-{4-[4-(2-hydroxy-2-methyl-propionyl)-benzyl]phenyl}-2-methyl-propan-1-one, 2-methyl-1-(4-methylthiophenyl)-2-morpholinopropan-1-one, 2-benzyl-2-dimethylamino-1-(4-morpholinophenyl)-butanone-1, and 2-(dimethylamino)-2-[(4-methylphenyl)methyl]-1-[4-(4-morpholinyl)phenyl]-1-butanone.

Examples of the acylphosphine oxide-type photopolymerization initiator include 2,4,6-trimethylbenzoyl-diphenyl-phosphine oxide and bis(2,4,6-trimethylbenzoyl)-phenyl-phosphine oxide.

Examples of the titanocene-type photopolymerization initiator include bis(η5-2,4-cyclopentadien-1-yl)-bis(2,6-difluoro-3-(1H-pyrrol-1-yl)-phenyl)titanium.

Examples of another photopolymerization initiator include 1,2-octanedione, 1-[4-(phenylthio)-2-(o-benzoyloxime)], ethanone, 1-[9-ethyl-6-(2-methylbenzoyl)-9H-carbazol-3-yl], 1-(o-acetyloxime), and a mixture of oxyphenyl acetic acid, 2-[2-oxo-2-phenylacetoxyethoxy]ethyl ester and oxyphenyl acetic acid, 2-(2-hydroxyethoxyl)ethyl ester.

Examples of a cation-type photopolymerization initiator include a mixture of iodonium, (4-methylphenyl)[4-(2-methylpropyl)phenyl]-hexafluorophosphate(1-), and propylene carbonate.

Examples of the polymerization accelerator include ethyl-4-dimethylaminobenzoate and 2-ethylhexyl-4-dimethylaminobenzoate.

A PVD method, a spin coat method, a printing method, a coating method, a spray method, a casting method, or the like is used to form the monomer layer 24.

Figure 7:
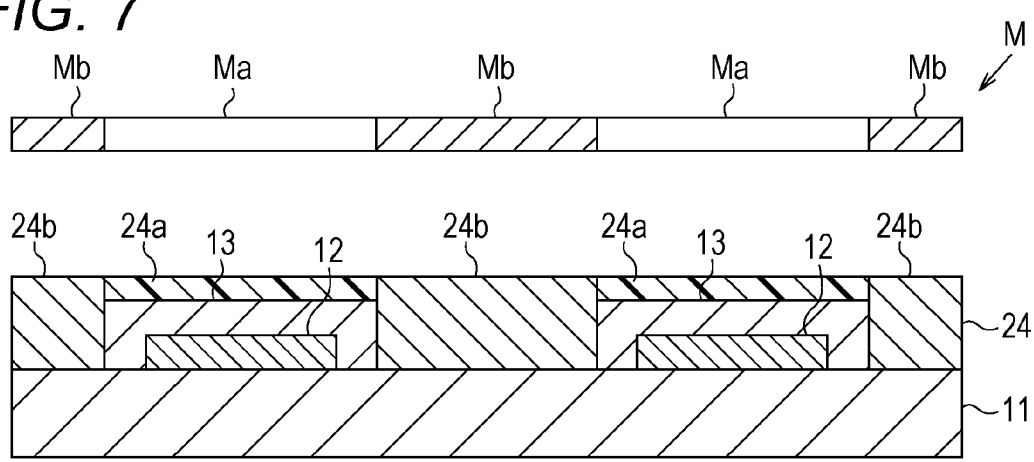
FIG. 7 is a cross-sectional elevation view for illustrating the method for manufacturing an organic semiconductor element according to the embodiment of this disclosure.

As illustrated in FIG. 7, the formed monomer layer 24 is irradiated with light. At this time, in a gap between the monomer layer 24 and a light source, a mask M which includes multiple regions whose light transmission characteristics are different from each other is disposed. The mask M, for example, includes a transmission part Ma which transmits light and a non-transmission part Mb which does not transmit light. The transmission part Ma in the mask M is disposed at a position to face a portion where the organic semiconductor layer 14 is formed. The non-transmission part Mb in the mask M is disposed at a position to face a portion where the organic semiconductor layer 14 is not formed. As long as only a predetermined portion in the monomer layer 24 is irradiated with light, the mask M may be omitted.

The light with which the monomer layer 24 is irradiated may be any one of infrared rays, visible rays, ultraviolet rays, ion beam, and radiation. When the monomer layer 24 is irradiated with light, the monomer layer 24 may be irradiated with multiple light beams having different wavelengths from each other at the same time or at different times. The monomer layer 24 may be irradiated with light multiple times at predetermined time intervals. When the monomer layer 24 is irradiated with light multiple times, an amount of light irradiation at one time may be the same as or different from each other. The whole mask M may be irradiated, at one time, with light with which the monomer layer 24 is irradiated. Alternatively, the whole mask M may be irradiated with light by scanning of light with which a part of the mask M is irradiated.

When the monomer layer 24 is irradiated with light which has passed through the transmission part Ma, a photopolymerizable unsaturated group generates a radical in an irradiation part 24a which has been irradiated with light in the monomer layer 24, and a polymerization reaction of a 6,12-dioxaanthanthrene derivative proceeds.

For example, when $R^3$ and $R^9$ are vinyl groups, and the other functional groups are independently hydrogen atoms, radical polymerization of a 6,12-dioxaanthanthrene derivative proceeds in accordance with reaction formula (3) as described below. In reaction formulae (3) to (8) as described below, the 6,12-dioxaanthanthrene is represented as PXX. In reaction formulae (3) to (8), PXX may be a 6,12-dioxaanthanthrene derivative in which $R^5$ and $R^{11}$ are non-photopolymerizable substituents and the other functional groups are independently hydrogen atoms. Also when any one of $R^1$ to $R^{11}$ (except $R^6$) is a vinyl group, and the other functional groups are independently hydrogen atoms, radical polymerization of the 6,12-dioxaanthanthrene derivative proceeds via a similar route, although the degree of crosslinking is lowered. Also when 6,12-dioxaanthanthrene and a vinyl group are bonded through an aromatic ring or a heteroaromatic ring, radical polymerization of the 6,12-dioxaanthanthrene derivative proceeds via a similar route.

[chemical formula 6]

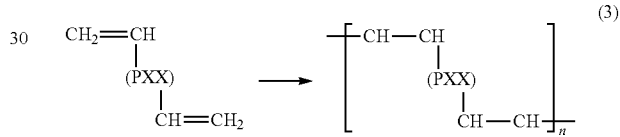

For example, when $R^3$ and $R^9$ are ethynyl groups, and the other functional groups are independently hydrogen atoms, radical polymerization of the 6,12-dioxaanthanthrene derivative proceeds in accordance with reaction formula (4) as described below. Also when any one of $R^1$ to $R^{11}$ (except $R^6$) is an ethynyl group, and the other functional groups are independently hydrogen atoms, radical polymerization of the 6,12-dioxaanthanthrene derivative proceeds via a similar route, although the degree of crosslinking is lowered. Also when 6,12-dioxaanthanthrene and an ethynyl group are bonded through an aromatic ring or a heteroaromatic ring, radical polymerization of the 6,12-dioxaanthanthrene derivative proceeds via a similar route.

[chemical formula 7]

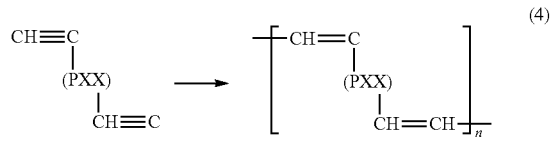

For example, when $R^3$ and $R^9$ are 1,3 butadiynyl groups, and the other functional groups are independently hydrogen atoms, radical polymerization of the 6,12-dioxaanthanthrene derivative proceeds in accordance with reaction formula (5) as described below. Also when any one of $R^1$ to $R^{11}$ (except $R^6$) is a 1,3 butadiynyl group, and the other functional groups are independently hydrogen atoms, radical polymerization of the 6,12-dioxaanthanthrene derivative proceeds via a similar route, although the degree of crosslinking is lowered. Also when 6,12-dioxaanthanthrene and a 1,3 butadiynyl group are bonded through an aromatic ring or a heteroaromatic ring, radical polymerization of the 6,12-dioxaanthanthrene derivative proceeds via a similar route.

[chemical formula 8]

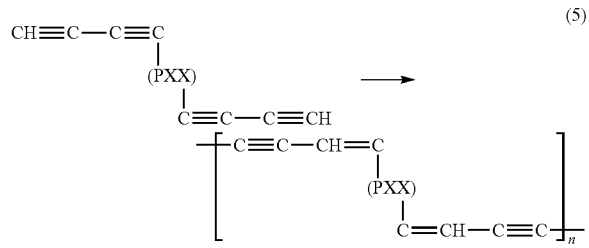
(5)

For example, when $R^3$ and $R^9$ are diazomethyl groups, and the other functional groups are independently hydrogen atoms, radical polymerization of the 6,12-dioxaanthanthrene derivative proceeds in accordance with reaction formula (6) as described below. Also when any one of $R^1$ to $R^{11}$ (except $R^6$) is a diazomethyl group, and the other functional groups are independently hydrogen atoms, at least formation of a 6,12-dioxaanthanthrene derivative dimer proceeds via a similar route. Also when 6,12-dioxaanthanthrene and a diazomethyl group are bonded through an aromatic ring or a heteroaromatic ring, radical polymerization of the 6,12-dioxaanthanthrene derivative proceeds via a similar route.

[chemical formula 9]

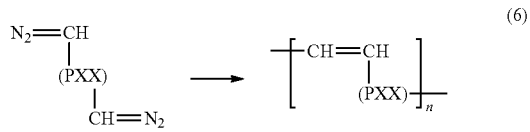
(6)

For example, when $R^3$ and $R^9$ are azido groups, and the other functional groups are independently hydrogen atoms, radical polymerization of the 6,12-dioxaanthanthrene derivative proceeds in accordance with reaction formula (7) as described below. Also when any one of $R^1$ to $R^{11}$ (except $R^6$) is an azido group, and the other functional groups are independently hydrogen atoms, at least formation of a 6,12-dioxaanthanthrene derivative dimer proceeds via a similar route. Also when 6,12-dioxaanthanthrene and an azido group are bonded through an aromatic ring or a heteroaromatic ring, radical polymerization of the 6,12-dioxaanthanthrene derivative proceeds via a similar route.

[chemical formula 10]

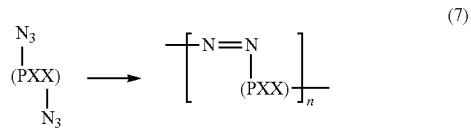
(7)

For example, when $R^3$ is an azido group, $R^9$ is an ethynyl group, and the other functional groups are independently hydrogen atoms, radical polymerization of the 6,12-dioxaanthanthrene derivative proceeds in accordance with reaction formula (8) as described below. Also when 6,12-dioxaanthanthrene and an azido group are bonded through an aromatic ring or a heteroaromatic ring, and also when 6,12-dioxaanthanthrene and an ethynyl group are bonded through an aromatic ring or a heteroaromatic ring, radical polymerization of the 6,12-dioxaanthanthrene derivative proceeds via a similar route.

[chemical formula 11]

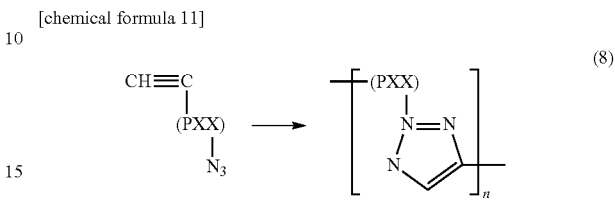
(8)

That is, the photopolymerizable unsaturated group illustrated above generates an organic semiconductor material which has a repeating unit of a 6,12-dioxaanthanthrene derivative represented by structural formula (2).

[chemical formula 12]

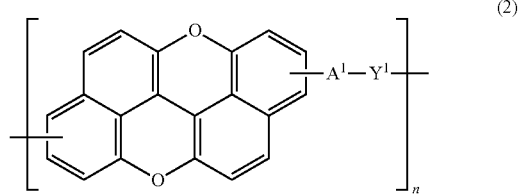
(2)

$A^1$ represents an aromatic ring, a heteroaromatic ring, or a direct bond. $Y^1$ represents anyone of a divalent alkene, a divalent alkyne, an azo group, and a 1,2,3-triazole ring.

As a result, in the irradiation part 24a, an organic semiconductor material which is a polymer of the 6,12-dioxaanthanthrene derivative is generated to decrease solubility to an organic solvent. Meanwhile, in a non-irradiation part 24b which is not irradiated with light in the monomer layer 24, a polymerization reaction of a 6,12-dioxaanthanthrene derivative does not proceed. Therefore, solubility to an organic solvent in the non-irradiation part 24b is higher than that in the irradiation part 24a.

Figure 8:
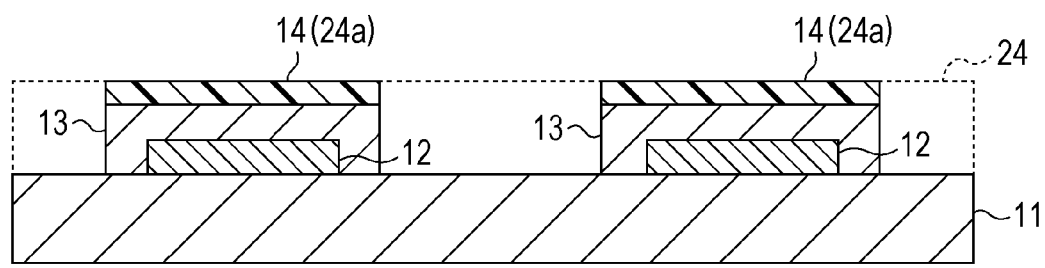
FIG. 8 is a cross-sectional elevation view for illustrating the method for manufacturing an organic semiconductor element according to the embodiment of this disclosure.

As illustrated in FIG. 8, when the irradiation part 24a is irradiated with light, an organic solvent is supplied to the monomer layer 24 to cause the monomer layer 24 to be developed. For development, a dip development method, a step paddle development method, a vibration development method, a reverse development method, a spray development method, a shower development method, or the like is used. Accordingly, the non-irradiation part 24b in the monomer layer 24 is removed from the substrate 11, and the irradiation part 24a remains on the substrate 11 as the organic semiconductor layer 14. As a result, a plurality of the organic semiconductor layers 14 is formed on the substrate 11.

In a part which has been irradiated with light in the monomer layer 24, a polymerization reaction of the 6,12-dioxaanthanthrene derivative proceeds. Therefore, compared with a structure in which molecules of a 6,12-dioxaanthanthrene derivative are not cross-linked with each other, resistance to mechanical deformation is improved in the organic semiconductor element 10 including the organic semiconductor layer 14.

When all of the monomer layers 24 formed on the substrate 11 are the organic semiconductor layers 14, development of the monomer layer 24 may be omitted. Alternatively, instead of development, patterning of the organic semiconductor layer 14 may be performed by photolithography and etching. In this case, the whole monomer layer 24 may be irradiated with light, or a part of the monomer layer 24 may be irradiated with light. In patterning by etching, since a side wall or the like of the organic semiconductor layer 14 is exposed to an etchant more than a little, semiconductor characteristics of the organic semiconductor layer 14 may be degraded. Meanwhile, when the organic semiconductor layer 14 is formed through exposure to a 6,12-dioxaanthanthrene derivative, contact of an etchant with an organic semiconductor material which has a repeating unit of a 6,12-dioxaanthanthrene derivative structure is suppressed.

Figure 9:
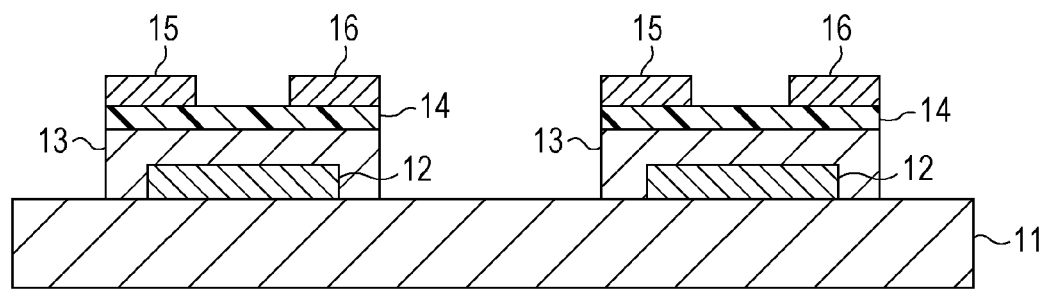
FIG. 9 is a manufacturing process view for illustrating the method for manufacturing an organic semiconductor element according to the embodiment of this disclosure.

As illustrated in FIG. 9, after the monomer layer 24 is developed, the source electrode 15 and the drain electrode 16 are formed on each organic semiconductor layer 14. A similar method to that for forming the gate electrode 12 is used to form the source electrode 15 and the drain electrode 16.

EXAMPLES

Example 1

A bottom-gate/top-contact type organic semiconductor transistor of Example 1 was formed in the following procedures. A gold thin film having a thickness of 100 nm was formed by a sputtering method on a silicon substrate on the surface of which a thermal oxide film had been formed. The pressure in a film-forming chamber was set to $5 \times 10^{-4}$ Pa when the gold thin film was formed. The power to be supplied to a gold target was set to 200 W. Then, photolithography and etching were performed for the gold thin film to form a gate electrode formed of gold.

Subsequently, a gate insulating layer formed of polymethylsilsesquioxane (hereinafter referred to as PMSQ) was formed on an entire surface of the substrate by a spin coat method. In the spin coat method, after the substrate was rotated at a rotational speed of 500 rpm for 5 seconds using a 10% isopropanol solution of PMSQ, the substrate was rotated at a rotational speed of 3000 rpm for 30 seconds using the 10% isopropanol solution of PMSQ A PMSQ film formed on the substrate was heated in the atmosphere at 150° C. for 30 minutes. Thereafter, a gate insulating layer covering each gate electrode was formed by performing photolithography and etching for the PMSQ film.

Subsequently, a monomer layer having a thickness of 50 nm was formed on the entire surface of the substrate by a vacuum deposition method with divinyl-6,12-dioxaanthanthrene. The monomer layer was formed at a deposition temperature of 300° C. and a deposition pressure of $2 \times 10^{-4}$ Pa.

The monomer layer was irradiated with light of 350 nm through a mask pattern formed with a glass substrate and a chromium pattern, and then a portion of the monomer which had not been irradiated with light was removed using an organic solvent. In this manner, an organic semiconductor layer covering each gate insulating film was formed.

Thereafter, a gold thin film having a thickness of 100 nm was formed on the whole substrate by a deposition method. Photolithography and etching were then performed for the gold thin film to independently form a source electrode and a drain electrode on the organic semiconductor layer.

In Example 1, it was found that an electron mobility at a gate length of 100 μm was 1.1 cm$^2$/Vs. Meanwhile, in Comparative Example 1 in which patterning with light irradiation was not performed for an organic semiconductor element, it was found that an electron mobility at a gate length of 100 μm was 1.0 cm$^2$/Vs.

As described above, it was found that the electron mobility as a characteristic of an organic semiconductor layer was not affected by patterning of the organic semiconductor layer with light irradiation.

Example 2

In Example 2, a bottom-gate/top-contact type organic semiconductor transistor was formed by changing only the forming material of the organic semiconductor layer from Example 1. That is, in Example 2, a monomer layer having a thickness of 50 nm was formed on the entire surface of the substrate by a vacuum deposition method with dialkynyl 6,12-dioxaanthanthrene. The organic semiconductor layer was formed at a deposition temperature of 330° C. and a deposition pressure of $2 \times 10^{-4}$ Pa.

In Example 2, it was found that an electron mobility at a gate length of 100 μm was 1.4 cm$^2$/Vs. Meanwhile, in Comparative Example 2 in which patterning with light irradiation was not performed for an organic semiconductor element, it was found that an electron mobility at a gate length of 100 μm was 1.1 cm$^2$/Vs.

As described above, as in Example 1, it was found that the electron mobility as a characteristic of an organic semiconductor layer was not affected by patterning of the organic semiconductor layer with light irradiation. In addition, it was found that the electron mobility in a 6,12-dioxaanthanthrene derivative into which a dialkynyl group having a triple bond was introduced was higher than that in a 6,12-dioxaanthanthrene derivative into which a vinyl group having a double bond was introduced in Example 1. That is, it was found that the electron mobility of the organic semiconductor layer was increased by a π conjugation bond formed by a photopolymerization reaction with a triple bond.

Example 3

In Example 3, a bottom-gate/top-contact type organic semiconductor transistor was formed by changing only the forming material of the organic semiconductor layer from Example 1. That is, in Example 3, a monomer layer was formed with dialkynyl 6,12-dioxaanthanthrene and 2,2-dimethoxy-1,2-diphenylethan-1-one as an alkylphenone type-photopolymerization initiator. The dialkynyl 6,12-dioxaanthanthrene was deposited on the substrate at a deposition temperature of 330° C. and a deposition pressure of $2 \times 10^{-4}$ Pa.

The 2,2-dimethoxy-1,2-diphenylethan-1-one was deposited on the substrate at a deposition temperature of 200° C. and a deposition pressure of $2 \times 10^{-4}$ Pa. The deposition speed of the dialkynyl 6,12-dioxaanthanthrene and the deposition speed of the 2,2-dimethoxy-1,2-diphenylethan-1-one were controlled so that the dialkynyl 6,12-dioxaanthanthrene film contained 5% of 2,2-dimethoxy-1,2-diphenylethan-1-one.

In Example 3, it was found that an electron mobility at a gate length of 100 μm was 1.2 cm$^2$/Vs. Meanwhile, in Comparative Example 3 in which patterning with light irradiation was not performed for an organic semiconductor element, it was found that an electron mobility at a gate length of 100 μm was 1.1 cm$^2$/Vs.

As described above, as in Example 1, it was found that the electron mobility as a characteristic of an organic semiconductor layer was not affected by patterning of the organic semiconductor layer with light irradiation.

Example 4

In Example 4, a bottom-gate/top-contact type organic semiconductor transistor was formed by changing the forming material and the forming method of the organic semiconductor layer from Example 1. That is, in Example 4, a monomer layer was formed on the entire surface of the substrate by a spin coat method with divinyl 6,12-dioxaanthanthrene. In the spin coat method, a 5% toluene solution of divinyl 6,12-dioxaanthanthrene was used.

In Example 4, it was found that an electron mobility at a gate length of 100 μm was 1.1 $cm^2$/Vs. Meanwhile, in Comparative Example 4 in which patterning with light irradiation was not performed for an organic semiconductor element, it was found that an electron mobility at a gate length of 100 μm was 1.0 $cm^2$/Vs.

As described above, as in Example 1, it was found that the electron mobility as a characteristic of an organic semiconductor layer was not affected by patterning of the organic semiconductor layer with light irradiation. In addition, the electron mobility of the organic semiconductor layer in Example 4 was the same as that of the organic semiconductor layer in Example 1. Therefore, it was found that the electron mobility of the organic semiconductor layer formed by the spin coat method was the same as that of the organic semiconductor layer formed by the deposition method.

The organic semiconductor element may be appropriately changed as described below.

First Modification Example

Figure 10:
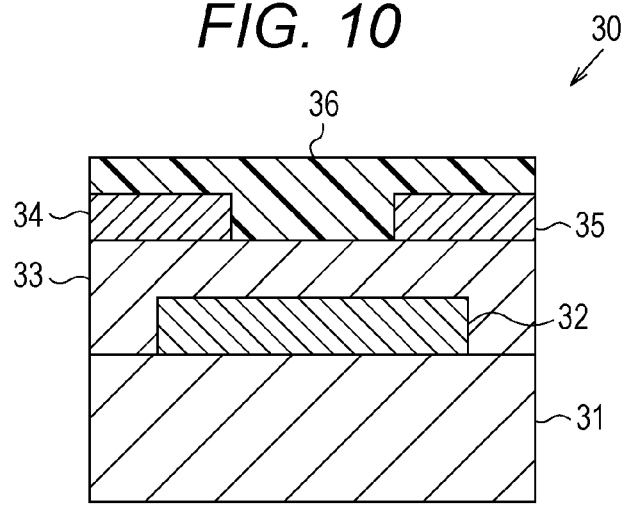
FIG. 10 is a cross-sectional view illustrating a cross-sectional structure in a first modification example of a semiconductor element.

As illustrated in FIG. 10, in an organic semiconductor element 30, a whole gate electrode 32 formed on a part of a substrate 31 is covered with a gate insulating layer 33. Unlike in the above-described embodiment, a source electrode 34 and a drain electrode 35 are independently formed on parts of the gate insulating layer 33. On the gate insulating layer 33, an organic semiconductor layer 36 is formed. The organic semiconductor layer 36 covers an upper surface of the source electrode 34 and an upper surface of the drain electrode 35, and fills a gap between the source electrode 34 and the drain electrode 35. The organic semiconductor element 30 is a bottom-gate/bottom-contact type organic semiconductor transistor.

Second Modification Example

Figure 11:
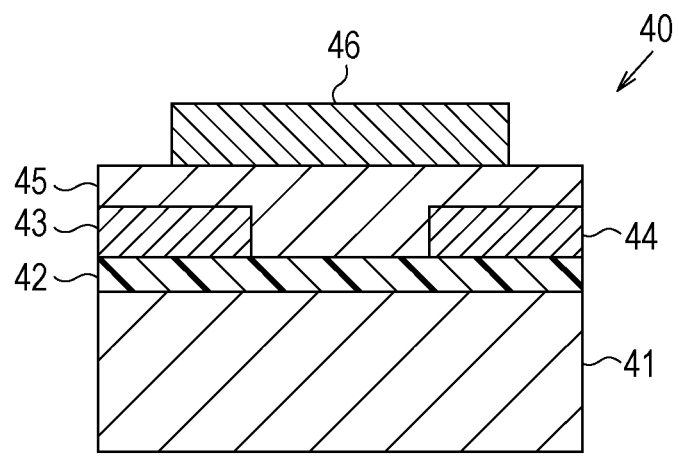
FIG. 11 is a cross-sectional view illustrating a cross-sectional structure in a second modification example of a semiconductor element.

As illustrated in FIG. 11, in an organic semiconductor element 40, unlike in the above-described embodiment, an entire upper surface of a substrate 41 is covered with an organic semiconductor layer 42. A source electrode 43 and a drain electrode 44 are independently formed on parts of the organic semiconductor layer 42. On the organic semiconductor layer 42, a gate insulating layer 45 is formed. The gate insulating layer 45 covers an upper surface of the source electrode 43 and an upper surface of the drain electrode 44, and fills a gap between the source electrode 43 and the drain electrode 44. A gate electrode 46 is laminated on a part of the gate insulating layer 45. The organic semiconductor element 40 is a top-gate/top-contact type organic semiconductor transistor.

Third Modification Example

Figure 12:
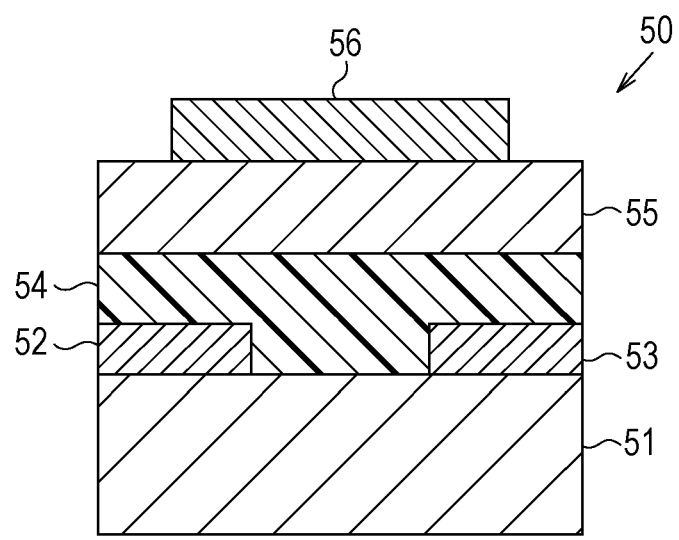
FIG. 12 is a cross-sectional view illustrating a cross-sectional structure in a third modification example of a semiconductor element.

As illustrated in FIG. 12, in an organic semiconductor element 50, a source electrode 52 and a drain electrode 53 are independently formed on parts of a substrate 51. On the substrate 51, an organic semiconductor layer 54 is formed. The organic semiconductor layer 54 covers an upper surface of the source electrode 52 and an upper surface of the drain electrode 53, and fills a gap between the source electrode 52 and the drain electrode 53. The whole organic semiconductor layer 54 is covered with a gate insulating layer 55. A gate electrode 56 is laminated on a part of the gate insulating layer 55. The organic semiconductor element 50 is a top-gate/bottom-contact type organic semiconductor transistor.

According to the above-described embodiment, the following effects are obtained.

A characteristic as a semiconductor is obtained by polymerization of a 6,12-dioxaanthanthrene derivative. Therefore, in an organic semiconductor element including a polymer of a 6,12-dioxaanthanthrene derivative as an organic semiconductor layer, resistance to mechanical deformation is improved.

Since an organic semiconductor layer is formed through exposure to a 6,12-dioxaanthanthrene derivative, contact of an etchant with an organic semiconductor material which has a repeating unit of a 6,12-dioxaanthanthrene derivative structure is suppressed.

A photopolymerizable unsaturated group contains a triple bond. Therefore, in a polymer of a 6,12-dioxaanthanthrene derivative, a π conjugation system is easily formed between 6,12-dioxaanthanthrenes which are different from each other.

Since $R^3$ and $R^9$ contain a photopolymerizable unsaturated group, steric hindrance caused by the photopolymerizable unsaturated group is suppressed in synthesis of a 6,12-dioxaanthanthrene derivative. In addition, in a polymer of a 6,12-dioxaanthanthrene derivative, a π conjugation system is easily formed between 6,12-dioxaanthanthrenes which are different from each other.

Since at least one of an aromatic ring and a heteroaromatic ring is interposed between a photopolymerizable unsaturated group and 6,12-dioxaanthanthrene, a π conjugation system is easily extended in a 6,12-dioxaanthanthrene derivative.

The 6,12-dioxaanthanthrene derivative in this disclosure can have the following structures.

(1) A 6,12-dioxaanthanthrene derivative represented by structural formula (1):

[chemical formula 13]

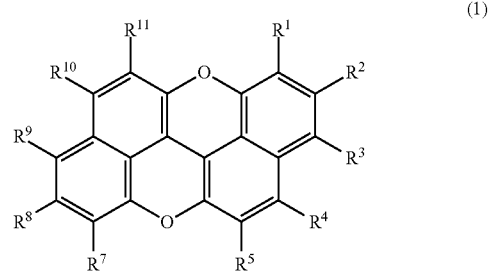

(1)

$R^3$ and $R^9$ are photopolymerizable unsaturated groups. $R^5$ and $R^{11}$ are non-photopolymerizable substituents.

(2) The 6,12-dioxaanthanthrene derivative according to the above (1), the photopolymerizable unsaturated group containing at least one triple bond.

(3) The 6,12-dioxaanthanthrene derivative according to the above (1), the photopolymerizable unsaturated group being anyone of an alkenyl group, an alkynyl group, a diynyl group, a methacrylic group, an ethyl methacrylic group, a diazo group, and an azido group.

(4) The 6,12-dioxaanthanthrene derivative according to any one of the above (1) to (3), the photopolymerizable unsaturated group being any one of an alkynyl group, a diynyl group, a diazo group, and an azido group.

(5) The 6,12-dioxaanthanthrene derivative according to any one of the above (1) to (4), the photopolymerizable unsaturated group being bonded to 6,12-dioxaanthanthrene via at least one of an aromatic ring and a heteroaromatic ring.

This application claims the benefit of priority based on Japanese Patent Application No. 2012-199497 filed on Sep. 11, 2012, the entire contents of which are incorporated herein by reference.

A person skilled in the art can conceive of various modifications, combinations, sub-combinations, and changes, in accordance with design requirements and other factors. It is understood that these modifications, combinations, sub-combinations, and changes are included in the gist of the appended claims and the scope of equivalents thereof.

What is claimed is:

1. A 6,12-dioxaanthanthrene derivative represented by structural formula (1):

[chemical formula 1]

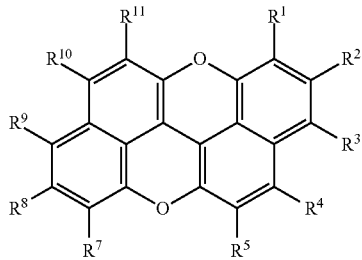

(1)

where $R^3$ and $R^9$ are photopolymerizable unsaturated groups, and $R^5$ and $R^{11}$ are non-photopolymerizable substituents.

2. The 6,12-dioxaanthanthrene derivative according to claim 1, wherein the photopolymerizable unsaturated group contains at least one triple bond.

3. The 6,12-dioxaanthanthrene derivative according to claim 1, wherein the photopolymerizable unsaturated group is any one of an alkenyl group, an alkynyl group, a diynyl group, a methacrylic group, an ethyl methacrylic group, a diazo group, and an azido group.

4. The 6,12-dioxaanthanthrene derivative according to claim 2, wherein the photopolymerizable unsaturated group is any one of an alkynyl group, a diynyl group, a diazo group, and an azido group.

5. The 6,12-dioxaanthanthrene derivative according to claim 1, wherein the photopolymerizable unsaturated group is bonded to 6,12-dioxaanthanthrene through at least one of an aromatic ring and a heteroaromatic ring.

6. An organic semiconductor element comprising an organic semiconductor layer, wherein the organic semiconductor layer includes a polymer of a 6,12-dioxaanthanthrene derivative represented by structural formula (1):

[chemical formula 2]

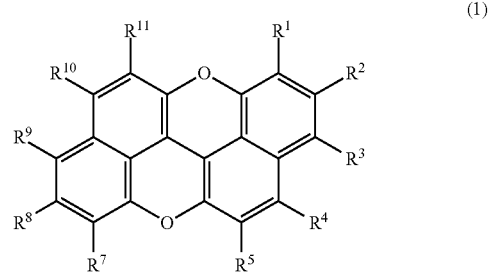

(1)

where $R^3$ and $R^9$ are photopolymerizable unsaturated groups, and $R^5$ and $R^{11}$ are non-photopolymerizable substituents.

7. An organic semiconductor element comprising an organic semiconductor layer, wherein the organic semiconductor layer includes an organic semiconductor material which has a repeating unit of a 6,12-dioxaanthanthrene derivative represented by structural formula (2):

[chemical formula 3]

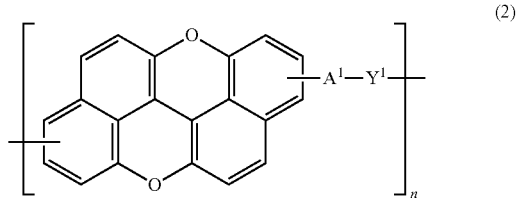

(2)

where $A^1$ represents an aromatic ring, a heteroaromatic ring, or a direct bond, and $Y^1$ represents any one of a divalent alkene, a divalent alkyne, an azo group, and a triazole ring.

8. A method for manufacturing an organic semiconductor element, comprising:

forming a monomer layer; and
irradiating the monomer layer with light to form an organic semiconductor layer,
wherein the monomer layer includes a 6,12-dioxaanthanthrene derivative represented by structural formula (1):

[chemical formula 4]

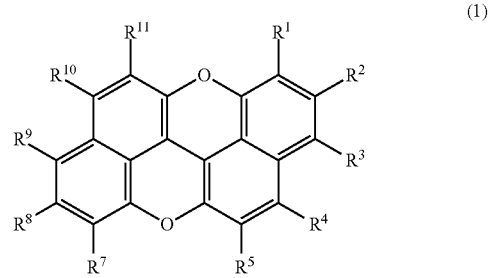

(1)

where $R^3$ and $R^9$ are photopolymerizable unsaturated groups, and $R^5$ and $R^{11}$ are non-photopolymerizable substituents.

9. The method for manufacturing an organic semiconductor element according to claim 8, wherein, when the monomer layer is irradiated with light, a part of the monomer layer is irradiated with the light, and a portion of the monomer layer which has not been irradiated with the light is removed to form the organic semiconductor layer.

* * * * *